(54) ULTRASONIC PLANTAR FASCIITIS THERAPY: APPARATUS AND METHOD

(76) Inventors: Jonathan J. Kaufman, 112 Willow St. Suite 1A, Brooklyn, NY (US) 11201; Alessandro Chiabrera, Viale Cambiaso 1/15, 16145 Genoa (IT); David Strom, 341 Tamasoa Pl., Castle Rock, CO (US) 80104

( * ) Notice: Subject to any disclaimer, the term of this patent is extended or adjusted under 35 U.S.C. 154(b) by 0 days.

(21) Appl. No.: 09/310,401

(22) Filed: May 12, 1999

(51) Int. Cl.[7] .................................................. A61B 17/22
(52) U.S. Cl. ............................................................. 601/2
(58) Field of Search ........................... 601/2, 3; 600/439; 607/51

(56) References Cited

U.S. PATENT DOCUMENTS

| | | |
|---|---|---|
| 3,828,769 * | 8/1974 | Mettler ....................................... 601/2 |
| 4,168,585 | 9/1979 | Gleichner . |
| 4,530,360 | 7/1985 | Duarte . |
| 5,003,965 | 4/1991 | Talish et al. . |
| 5,186,162 | 2/1993 | Talish et al. . |
| 5,211,160 | 5/1993 | Talish et al. . |
| 5,309,808 | 5/1994 | Kaufman et al. . |
| 5,429,117 | 7/1995 | McNamara et al. . |
| 5,458,130 | 10/1995 | Kaufman et al. . |
| 5,547,459 | 8/1996 | Kaufman et al. . |
| 5,549,544 * | 8/1996 | Young et al. ............................. 601/2 |
| 5,556,372 | 9/1996 | Talish et al. . |
| 5,558,623 | 9/1996 | Cody . |
| 5,578,060 | 11/1996 | Pohl et al. . |
| 5,611,153 | 3/1997 | Fisher et al. . |
| 5,626,554 | 5/1997 | Ryaby et al. . |
| 5,718,673 | 2/1998 | Shipstead . |
| 5,730,705 | 3/1998 | Talish et al. . |
| 5,741,317 * | 4/1998 | Ostrow ...................................... 607/85 |
| 5,762,616 | 6/1998 | Talish et al. . |
| 5,776,090 | 7/1998 | Bergman et al. . |
| 5,799,659 | 9/1998 | Stano . |

OTHER PUBLICATIONS

Lowell H. Gill et al, "Outcome of Nonsurgical Treatment for Plantar Faciitis", *Foot & Ankle International*, 1996, vol. 17, No. 9, pp. 527–532.

Therapeutic Heat and Cold, Ed. by Justus F. Lehman, Williams & Wilkins, Fourth Edition, 1990, pp. 505–581.

Ossa Tron Update, Health Tronics, Inc., Marietta, GA, Pres release, 1996/1997.

"Shock Wave Devices for FDA Trials for Tissue Repair, Bone Healing", *Orthopedics Today*, 1997, vol. 17, No. 12.

* cited by examiner

Primary Examiner—Brian L. Casler
(74) Attorney, Agent, or Firm—Rader, Fishman & Grauer PLLC

(57) ABSTRACT

Non-invasive therapeutic treatment of plantar fasciitis in vivo using ultrasound is performed by subjecting a foot locale to an ultrasound signal supplied to an ultrasound transducer placed on the skin, and involving a repetitive finite duration signal consisting of plural frequencies that are in the ultrasonic range to 10 MHz. The ultrasound transducer is reproducibly positioned using an ultrasound fixture. The ultrasound signal is applied daily at least twice per day for 40 minutes per treatment, and has a power intensity (SATA) of 18 mW/cm$^2$. In an alternative embodiment, an orthotic device holds the foot in dorsiflexion concomitant with ultrasound treatment.

31 Claims, 4 Drawing Sheets

ULTRASONIC PLANTAR FASCIITIS THERAPY: APPARATUS AND METHOD

FIELD OF THE INVENTION

The invention pertains generally to apparatus and method for non-invasive at-home ultrasound treatment of enthesopathies in vivo. In particular, the invention pertains to apparatus and method for non-invasive at-home ultrasound treatment of plantar fasciitis in vivo.

BACKGROUND OF THE INVENTION

In recent years, various attempts have been made to treat plantar fasciitis. These approaches have not been particularly successful, and as a consequence have resulted in patients experiencing protracted periods of pain and discomfort. In addition, because of the very limited success of the treatment options available, physicians are unclear as to which option (for example, surgical or non-surgical) to pursue.

Plantar fasciitis is an inflammation of the plantar fascia, a ligament which is attached at one end to the inner tubercle of the heel bone. The plantar fascia extends from the heel bone, becoming broader and thinner as it runs longitudinally along the bottom of the foot, eventually dividing into 5 processes which connect to each of the five toes. There is no clear understanding of the exact cause(s) of inflammation in the plantar fascia. Some data point to the occurrence of heel spurs where the plantar fascia is attached to the calcaneus (heel bone), which themselves may be due to constant stretching of the fascia.

A number of issued patents disclose methods and apparatuses to treat plantar fasciitis by using a biomechanical approach. Generally speaking, the biomechanical methods attempt to position the patient's foot and leg for some period of time (often at night when the patient is asleep) in such a way so as to slightly stretch the plantar fascia, as a means by which the plantar fasciitis may eventually be relieved. For example, Bergmann et al. U.S. Pat. No. 5,776,090, disclose method and device for treating plantar fasciitis by placing a splint on the dorsal aspect of a patient's foot, ankle and foreleg, and holding the patient's foot, toes and ankle in the dorsiflexed position. The inventors state that stretching the patient's plantar fascia reduces symptoms over time.

Stano, U.S. Pat. No. 5,799,659 discloses an ankle foot orthosis night splint for treating plantar fasciitis. The disclosed orthosis is a rigid, molded shell having a generally U-shaped cross-sectional configuration and a flat foot bed. The orthosis is covered by a soft-fabric, and uses a removable and interchangeable foot bed wedge insert which permits the angle of dorsiflexion and the amount of plantar-flexion to be varied.

Shipstead, U.S. Pat. No. 5,718,673 discloses foot supporting devices and methods to hold the wearer's foot and leg at a predetermined angle for sufficient time to reduce foot fatigue or pain, while the wearer is not on the feet.

Gleichner, U.S. Pat. No. 4,168,585 discloses a one-piece heel cushion formed of homogeneous elastomeric material adapted to conform to the insole of a wearer's shoe to relieve heel pain. The cushion tapers toward its forward end and has an elongated cavity in the lower surface extending directly under the heel bone.

Fisher et al., U.S. Pat. No. 5,611,153 disclose an insole and a method for relieving bottom of heel pain (i.e., plantar heel pain). The insole, which is removable, is comprised of a flexible, shock-absorbing material, and is tapered downward from the arch portion.

An excellent description of biomechanical and other non-surgical methods for treating plantar fasciitis can be found in the published journal article entitled "Outcome of nonsurgical treatment for plantar fasciitis," by L H Gill and G M Kiebzak, appearing in *Foot and Ankle Int*, September 1996, Volume 17, Number 9, pages 527–532. The authors report on the use of short leg walking cast, steroid injection, rest, ice, runner's shoe, crepe-soled shoe, aspirin or non-steroidal anti-inflammatory drug, heel cushion, low-profile plastic heel cup and heat, to treat plantar fasciitis. They found that most of the treatments were unpredictable or minimally effective.

Surgical treatments for plantar fasciitis have also been proposed, usually as a last resort, as these methods can have associated with them a variety of complications, including foot numbness, protracted post-operative pain and discomfort, skin incision problems or painful scars on the bottom of the foot. Endoscopic surgery has also been described. For example, McNamara et al., U.S. Pat. No. 5,429,117 disclose a method and system for performing endoscopic surgery at locations where tissue inserts into bone, as for example with the plantar fascia.

Physical therapy based on ultrasound methods have also been used for treatment of plantar fasciitis, with the therapeutic benefits assumed to result from the production of heat within the body. An excellent reference for such techniques can be found in the book *Therapeutic Heat and Cold, Fourth Edition*, edited by Justus F. Lehmann and published by Williams and Wilkins of Baltimore, Md. in 1990. Although ultrasound based physical therapy is widely used, mostly for deep heating of muscles (to provide relief from the effects associated with spasms) and for relief from joint pain, it apparently has been utilized much less frequently for the treatment of plantar fasciitis, and when it has, little success has been achieved. When prescribed for the treatment of plantar fasciitis, ultrasound therapy is applied by a physical therapist to a patient in a relatively uncontrolled way (i.e., the therapist applies the ultrasound in an ad hoc fashion), at relatively high power intensities (e.g., at or above 1 Watt/$cm^2$) for short periods (about 5 minutes) only 2–3 times per week at most.

Numerous ultrasound therapy devices have been described. For example, Cody, U.S. Pat. No. 5,558,623 discloses a therapeutic ultrasonic device which transmits multiple ultrasonic frequencies through a single ultrasound applicator. The applicator is hand-held by a specially trained therapist during treatment of a patient at a particular anatomical site, usually at ultrasound spatial-average temporal-average (SATA) intensities of 1 Watt per square centimeter or more. Because of the relatively high intensities used, a "stroking" technique is almost always utilized. A similar device, also applied by a physical therapist, is described by Pohl et al., U.S. Pat. No. 5,578,060, which discloses a reconfigurable physical therapy apparatus and a method of providing operator-selected stimuli to a patient.

Several other ultrasound methods and devices relating primarily to bone growth and repair have also been described. For example, Kaufman et al., U.S. Pat. No. 5,309,808 disclose apparatus and method for therapeutically treating and/or quantitatively evaluating bone tissue in vivo, by subjecting bone to an ultrasonic signal pulse of finite duration, and involving a composite sine-wave signal consisting of plural discrete frequencies. These frequencies are spaced in the ultrasonic region to approximately 2 MHz; the excitation signal is repeated substantially in the range 1 to 1000 Hz. In a closely related patent, Kaufman et al., U.S. Pat. No. 5,458,130, the same inventors extend the apparatus and method to the treatment to musculoskeletal tissue in general. In another patent by the same inventors, Kaufman et al., U.S. Pat. No. 5,547,459 disclose apparatus and method for therapeutically treating bone tissue in vivo, by subjecting bone to an ultrasonic sinusoidal signal pulse peculiarly modulated by a sinusoidal signal with a frequency between about 0 Hz and 25 kHz.

Duarte, U.S. Pat. No. 4,530,360 discloses apparatus and a method of using ultrasonic energy for therapeutic treatment of bone tissue in vivo, using a pulsed sine wave at substantially a single frequency within the range 1.3 to 2.0 MHz, and at a pulse repetition rate of 100 to 1000 Hz.

Talish, U.S. Pat. No. 5,762,616 discloses apparatus for ultrasonic treatment of sites corresponding to the torso. The apparatus includes means for positioning and holding an ultrasound treatment head module adjacent to positions of the body, such as the clavicle, the pelvis and the spine.

The prior art, exemplified by the references that have been briefly discussed, have used either biomechanical, ultrasonic or surgical approaches, for treating plantar fasciitis. The surgical option, while it can sometimes relieve patients of pain, has associated with it various side effects as well as high costs, and is generally chosen only as a last resort. Non-surgical approaches have not as yet been very successful in treating plantar fasciitis. However, the present inventors have discovered how to achieve much greater success with use of a non-surgical method using ultrasound in treating the pain and discomfort associated with plantar fasciitis.

BRIEF STATEMENT OF THE INVENTION

It is accordingly an object of the invention to provide an improved method and apparatus for therapeutically treating plantar fasciitis, whereby to eliminate or significantly reduce the associated pain and discomfort.

Another object is to meet the above object, such that plantar fasciitis may be more efficiently and more effectively treated than heretofore.

A further object is to demonstrate ultrasound treatment signals and regimens whereby to achieve the indicated objectives.

A further object is to achieve the above objects with apparatus and method that can be utilized at home, without the need for a specially trained therapist.

Another object is to treat not only plantar fasciitis, but heel pain generally and enthesopathies, at other anatomical sites, as well.

A specific object is to take advantage of the combination of both biomechanical and ultrasonic therapies whereby to achieve the indicated objectives.

It is a general object to achieve the foregoing objects with apparatus components that are for the most part commercially available.

Briefly stated, the invention in its presently preferred form achieves the foregoing objectives by iteratively subjecting the bottom of an affected foot to an ultrasonic signal of finite duration, consisting of frequency components in the ultrasonic region to approximately 10 MHz, delivered by a transducer placed on skin overlying the plantar fascia; the excitation signal is repeated in the range of 1 Hz to 15,000 Hz. The exposure time for ultrasonic therapy is chosen to be in the range of 20 minutes to 2 hours, for 1 to 3 times a day, for a period of days as necessary for resolving the pain and discomfort associated with plantar fasciitis. In the presently preferred embodiment of the invention, two ultrasound treatments, one in the morning and one in the evening, each lasting 40 minutes, and having an average power intensity (SATA) of 18 mW/cm$^2$, achieves the indicated objectives.

In the currently preferred embodiment, the ultrasonic signal is generated by a waveform synthesizer to which the transducer is connected via a power amplifier. The waveform synthesizer emits an electrical signal which is a pulsed sine wave with a frequency of about 3.5 MHz, the duration of the pulse on-time is 4.8 milliseconds, and the signal is repeated at a repetition rate of 15 Hz.

In the presently preferred embodiment of the invention, the transducer is rectangular in shape, having dimensions 8 cm by 4 cm, and is mounted in a fixture which sits on the floor, and into which the patient's foot to be treated is placed. An ultrasound gel is used to efficiently acoustically couple the ultrasound signal from the transducer into the foot. The foot is reproducibly positioned by the fixture so that the same approximate anatomical region is treated each time, and also to ensure that the affected portion of the plantar fascia, particularly the region where it attaches to the calcaneus, receives ultrasonic energy. The large area of the transducer (in comparison to those currently utilized for any kind of ultrasound therapy) which covers a large region of the foot, in conjunction with a relatively low power intensity, relatively long treatment time, and with multiple treatments repeated daily, as well as reproducible repositioning of the ultrasound transducer, all combine to offer significant and dramatic relief from the pain and discomfort associated with plantar fasciitis.

DETAILED DESCRIPTION OF THE INVENTION

Figure 1:
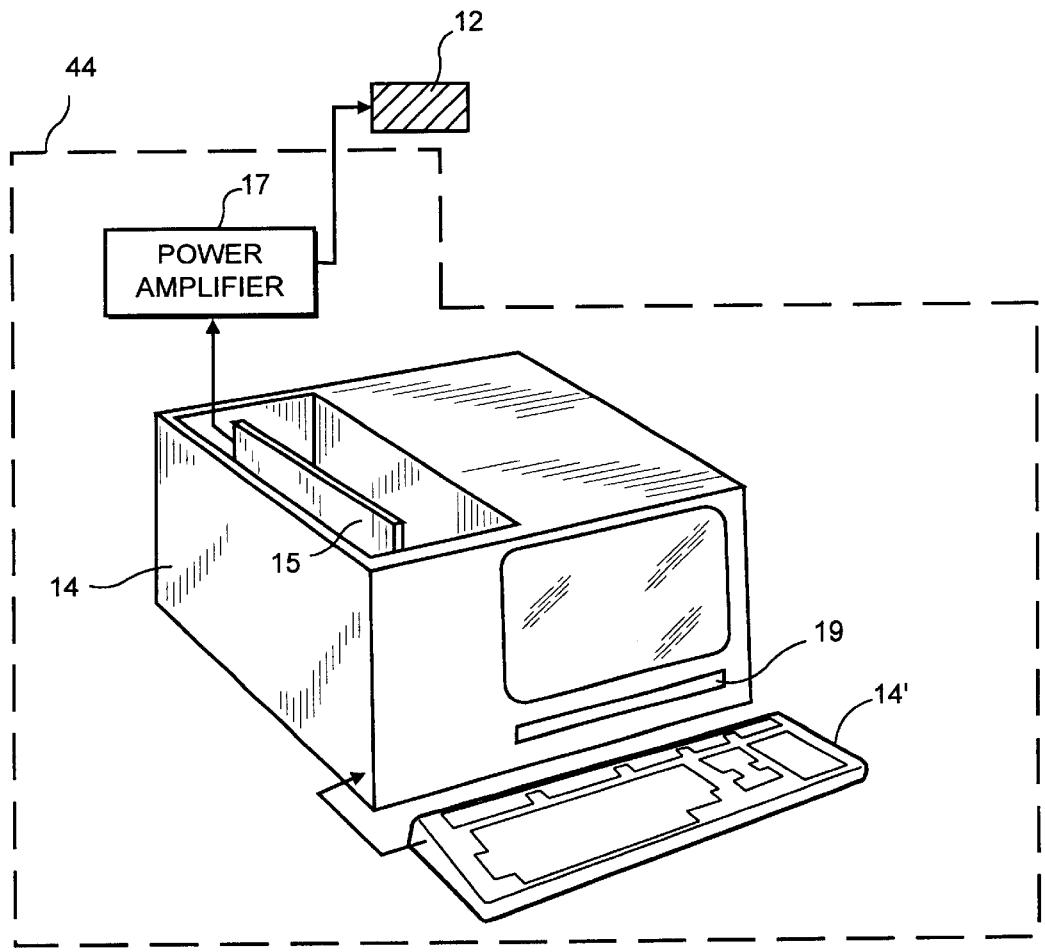
FIG. 1 is an electrical-circuit diagram schematically showing the interconnected relation of components of apparatus of the invention, including the ultrasound transducer and ultrasound pulser, in a currently preferred embodiment of the invention.
Figure 2:
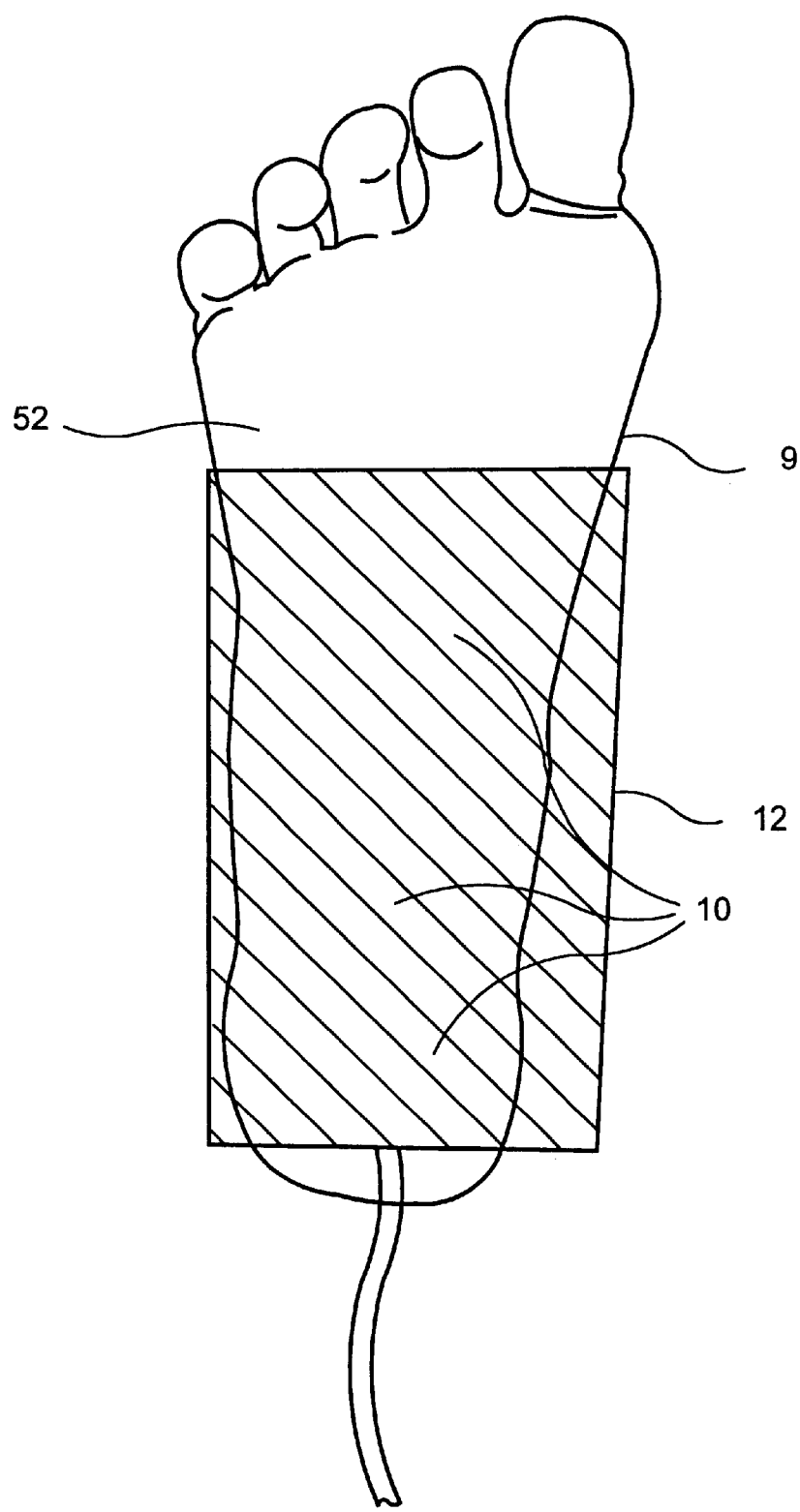
FIG. 2 is a diagram showing the ultrasound transducer placed against the skin of the bottom of the foot, in a currently preferred embodiment of the invention.
Figure 3:
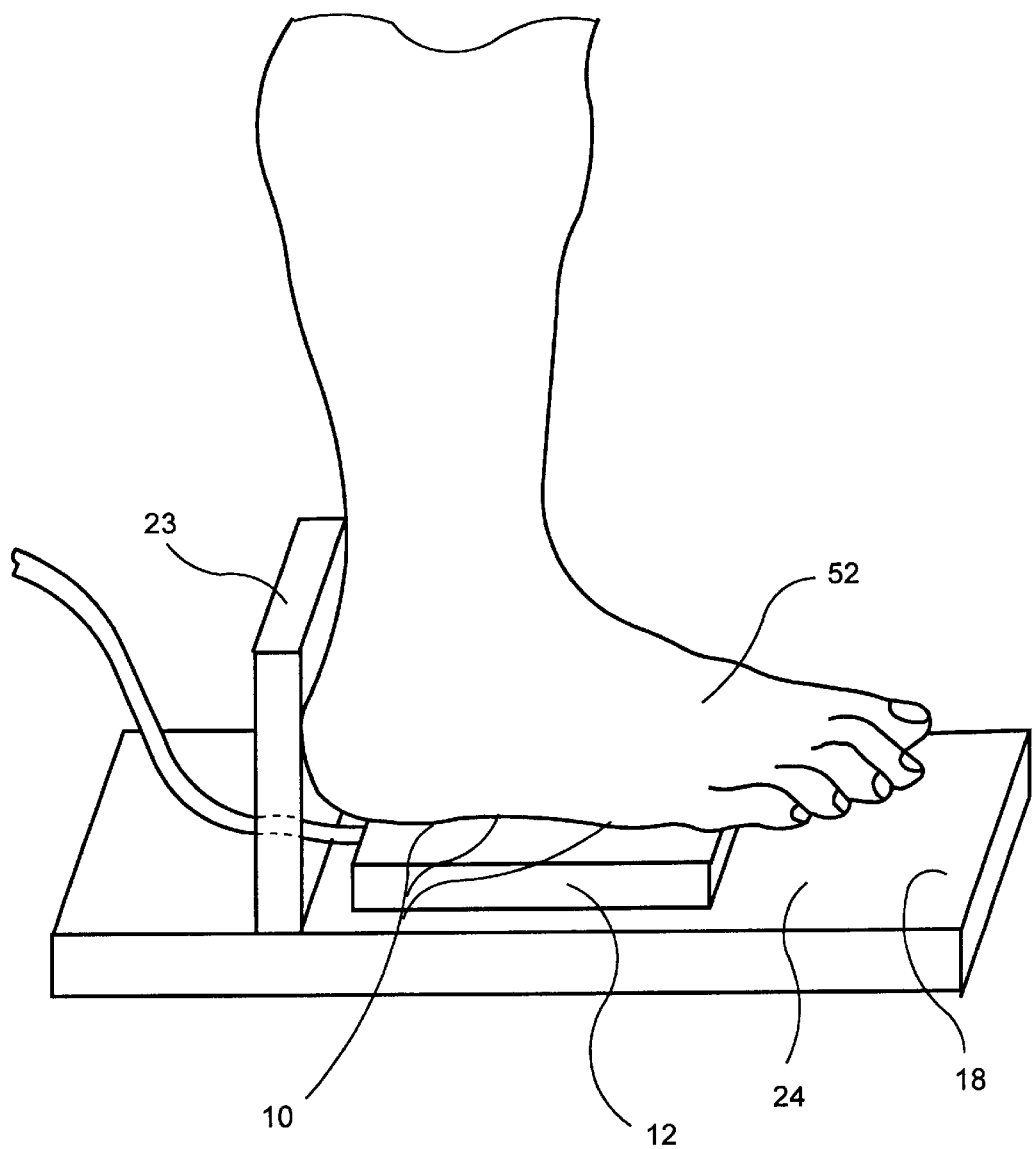
FIG. 3 is a diagram showing the ultrasound transducer, ultrasound fixture and foot, in a currently preferred embodiment of the invention.

The invention will be described in detail for a presently preferred embodiment, in conjunction with the accompanying drawings. The invention is shown in FIG. 1, FIG. 2 and FIG. 3, in application to interconnected components for constructing apparatus for performing methods of the invention, namely for therapeutically treating plantar fasciitis in vivo, whereby to reduce inflammation and associated pain and discomfort. These components are, in general, commercially available from different sources and will be identified before providing detailed description of their total operation.

In FIG. 2, the foot locale 10 of a patient's foot 52 to be treated is shown with skin 9 and to be placed next to an ultrasonic transducer 12, and obtainable from Acoustic Imaging, Inc., Phoenix, Ariz.; suitably, the transducer 12 may be comprised of a 4 centimeter by 8 centimeter rectangular air-backed PZT-5a piezoelectric element, and having a front layer matched for soft tissue, with a nominal center frequency of 3.5 MHz. As shown, transducer 12 is used for signal launching, in which the launched signal is transmitted through standard ultrasonic couplant, through the skin and overlying soft tissue (not shown), and into the plantar fascia (also not shown). The ultrasound couplant may suitably be obtained from Parker Laboratories, Incorporated, of Orange, N.J. In this way the ultrasound transducer may be understood to be efficiently acoustically coupled to the skin 9.

Now, with reference to FIG. 1, basic operation is governed by computer means 14, which may be a PC computer, such as the "500 MHz Pentium III" available from Gateway 2000, Inc., North Sioux City, S. Dak.; as its designation suggests, this computer contains a 500 MHz clock-pulse generator, and an Intel Pentium III microprocessor, with provision for keyboard instruction at 14'.

An electrical function-generator card 15 is relied upon to generate an excitation signal which is supplied to the launch transducer 12, via power amplifier means 17. The power amplifier is suitably Model No. 240L, an RF power amplifier product of EIN, Inc., Rochester, N.Y. This product provides a 50 dB gain, over the range 20 kHz to 10 MHz. The excitation signal generated by card 15 is a pulsed sine wave signal, having a frequency of 3.5 MHz, a pulse on time of 4.8 milliseconds, and a pulse repetition rate of 15 Hz; after input of this signal to power amplifier 17, the peak value of the output signal from the power amplifier 17 is approximately 24 volts. Card 15 may suitably be a waveform synthesizer product of Quatech, Inc., Akron, Ohio, identified by Quatech part No. WSB-100. This waveform synthesizer provides generation of analog signals independent of the host computer 14, allowing full processor power to be used for other tasks, including calculation of waveform data; it has the capacity to generate an output signal comprising literally thousands of points in the indicated frequency range. The computer 14, card 15, and power amplifier 17 may be understood to comprise an ultrasound pulser 44 (shown within the dashed line in FIG. 1); however its present embodiment as described herein has much more flexibility than conventional ultrasound pulsers because of the wide range of electrical excitation signals that may be realized. (It should nevertheless be understood that a more conventional ultrasound pulser may also be utilized in alternative embodiments of the present invention.)

With reference to FIG. 3, an ultrasound fixture 18 is also shown and receives the patient's foot 52 and holds it next to transducer 12. As may be seen, the foot 52 and transducer 12 are jointly held so that foot locale 10 may reproducibly be both re-positioned and ultrasonically treated. In the presently preferred embodiment, this is achieved by including in the fixture a transverse segment 23 upon which the posterior portion of the heel can rest, while the bottom portion of the foot rests on a longitudinal segment 24 of the fixture. The transducer 12 sits in a cut-out portion of longitudinal segment 24. In the presently preferred embodiment of the invention, the ultrasound fixture is made of Plexiglas, suitably available (including fabrication) from Industrial Plastic Supply Company, New York, N.Y. As may be seen, the transducer 12 faces up towards the bottom of the foot locale 10 to be treated.

Finally, and again with additional reference to FIG. 1, general signal-processing/display/storage software, for the signal processing control and operation of the computer 14 is not shown but will be understood to be a CD-ROM loaded at 19 into the computer; this software is suitably MATLAB 5, available from The MathWorks, Inc., Natick, Mass. Further software, also not shown include the Signal Processing, Optimization and Statistics Toolboxes, also available from MathWorks, as well as C++ Version 5, available from the Microsoft Corporation, Bothell, Wash.

In the presently preferred embodiment of the invention and with additional reference to FIG. 1, FIG. 2 and FIG. 3, a patient's foot 52 is placed into ultrasound fixture 18. The ultrasound transducer 12, connected to an ultrasound pulser 44, is placed adjacent to foot locale 10 with surrounding soft tissue and skin 9, with sufficient ultrasound gel to insure efficient acoustic coupling. An ultrasound signal is transmitted from transducer 12, passes through skin 9, soft tissue, and into the foot locale 10 containing the plantar fascia. The transmitted ultrasound signal is generated by pulsing the transducer with a 4.8 millisecond duration sine wave, repeating at 15 Hz. This produces an ultrasound signal with a center frequency of about 3.5 MHz, and of about 4.8 millisecond in duration, repeating at a frequency of 15 Hz. The power intensity (SATA) of the ultrasound signal impinging on the skin surface is 18 mW/cm$^2$.

In the presently preferred embodiment of the invention, the foot is placed in such a manner that a major portion of the plantar fascia receives ultrasound energy, including that portion which joins to the calcaneus. Further, the fixture serves to ensure that each treatment provides ultrasound stimulation to the same portion of the foot. In the presently preferred embodiment, the ultrasound signal is applied twice per day, once in the morning and once in the evening, with each treatment lasting for 40 minutes, for a number of days as required to resolve the pain and discomfort of plantar fasciitis. In the presently preferred embodiment, many cases resolve within 30 days of treatment as described hereinabove.

The preceding description has proceeded on the basis that ultrasound can heal the inflammation associated with plantar fasciitis. While there have been prior attempts to treat plantar fasciitis with ultrasound, they have not been successful. In contrast to these previously disclosed but unsuccessful treatment apparatuses and methods, the present invention relies on several key features: (1) reproducible positioning of a transducer so that the same region of the foot is treated each time; (2) large area transducer covering a large area of tissue; (3) low power intensity; (4) long treatment periods, in terms of minutes per treatment; (5) multiple intra-day treatments; and (6) daily treatments. These ultrasound treatment characteristics described hereinabove are able to achieve what has not been possible heretofore, namely the successful resolution of the inflammation, pain and discomfort of plantar fasciitis.

It should be understood that the ultrasound fixture serves not only as a convenient means to hold the transducer against the foot, but also provides a way in which a patient may be self-treated at home. Thus, the region to be treated cannot be arbitrarily chosen by the patient, but is instead pre-specified and pre-located by design. This, together with the relatively low power intensity makes home use both safe and efficacious.

It should also be appreciated that the present invention can be embodied with a variety of ultrasound signals, including continuous sinusoid, pulsed sinusoid, broadband repetitive pulses, frequency modulated sinusoids, and amplitude modulated sinusoids. Notwithstanding the variety of signals which can be utilized in the present invention, they should be applied relatively often (at least once a day, but twice or more a day are preferable), at relatively low power intensities (no more than 250 mW/cm$^2$ but 18 mW/cm$^2$ is preferable), with a relatively large transducer (with area at least 4 cm² but 32 cm² is preferable) in a fixture which ensures that the same region of the plantar fascia is treated from one treatment to the next, and wherein such positioning ensures that the portion of the plantar fascia which joins to the calcaneus is included. The treatment regimen should be repeated for as many days as necessary to achieve full healing.

Figure 4:
FIG. 4 is a diagram showing an orthotic splint, used in one of the alternative embodiments of the invention.

In an alternative embodiment of the invention, ultrasound therapy is applied concomitantly while the patient's foot is held in dorsiflexion. In this alternative embodiment, and with additional reference to FIG. 4, an orthotic device 26 is used to keep the foot in a position so that the plantar fascia is slightly extended. This slight extension, when combined with the ultrasound treatment, leads to more effective healing compared to when ultrasound is applied alone. A number of orthotic devices are known in the art. For example, Bergmann et al. U.S. Pat. No. 5,776,090, disclose a splint which is affixed on the dorsal aspect of a patient's foot, ankle and foreleg, which holds the patient's foot, toes and ankle in a dorsiflexed position, and which is incorporated by reference hereinto. Stano, U.S. Pat. No. 5,799,659 discloses another orthosis, which is incorporated by reference hereinto. Yet another orthosis or splint is disclosed by Shipstead, U.S. Pat. No. 5,799,659, and which is incorporated by reference hereinto. It should be appreciated that the present invention may include any orthosis which is capable of maintaining a patient's foot in dorsiflexion during ultrasound therapy. It should be further recognized that the ultrasound transducer, pulser and fixture (not shown in FIG. 4) may be combined with the orthosis into a single structure, or may instead remain as separate structures. It should also be understood that all of the variations with respect to ultrasound signals and treatment regimens disclosed hereinabove apply also to the embodiments of the invention which combine orthotic and ultrasound treatments. It should lastly be understood that the various embodiments of the invention disclosed herein may be utilized so that the patient is treated in a variety of positions, for example sitting or lying down. In each case, modifications of the ultrasound fixture or orthotic device may be necessary to permit the patient to have his or her required degree of freedom.

In yet an additional embodiment of the present invention, ultrasound treatment is combined with injection of a local anesthetic. In a presently preferred alternative embodiment, the local anesthetic is most suitably Marcaine, available from Schering Corporation, located in Kentworth, N.J. In this embodiment of the invention, 1 cc of Marcaine is injected into the origin of the plantar fascia on the calcaneus. Treatment with local anesthetic is combined with ultrasound according to the methods disclosed herein, and has been found to greatly aid in the resolution of the pain and discomfort associated with plantar fasciitis. In another embodiment of the invention, a non-steroidal anti-inflammatory cream is applied topically to the skin surface overlying the plantar fascia on the bottom of the foot. In this alternative embodiment, the non-steroidal anti-inflammatory cream is most suitably Ibuprofen cream, available from ITC Corporation, located in Denver, Colo. It should be understood that the cream is rubbed into the skin, and ultrasound therapy, according to the methods disclosed herein, is applied, preferably within 1 hour. The ultrasound, when used in conjunction with the cream, has been found to dramatically enhance the efficacy of either treatment acting alone. The enhancement in efficacy is due to a number of factors, including the ability of the ultrasound to propel the active ingredients in the cream towards the site of inflammation, which is generally many millimeters below the skin surface.

It should be additionally understood that a variety of creams and compounds may be utilized, either by local injection or by topical skin application, including, for example, corticosteroids, local anesthetics or non-steroidal anti-inflammatory creams. It should also be appreciated that the creams may serve a dual purpose, that is to reduce pain but also as a means to efficiently couple the ultrasound signal into the body, obviating the need for a separate application of an ultrasound coupling gel. It should lastly be further appreciated that the use of the creams and other compounds may be further combined not just with ultrasound, but with orthotic treatment as well, to further enhance the beneficial effects obtained.

Finally, it should be appreciated that while new methods and apparatuses for therapeutically treating plantar fasciitis have been disclosed herein, the treatments can be also applied to similar conditions arising at other anatomical sites within the body. Such similar conditions may be understood to fall under the general category of enthesopathies, and may include, for example, Achilles tendinitis, lateral epicondylitis and patellar tendinitis, as well as plantar heel pain but not necessarily diagnosed specifically as plantar fasciitis. Such conditions can also greatly benefit from the ultrasound treatment (and combined orthotic and anesthetic, non-steroidal anti-inflammatory creams or cortico-steroids) regimens disclosed herein.

While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

It will be seen that the described invention meets all stated objectives as to therapeutic treatment in vivo of plantar fasciitis specifically and heel pain and enthesopathies generally, with specific advantages that include but are not limited to the following:

(1) Significantly enhanced healing effects due to the reproducible repositioning of a large ultrasound transducer, as well as because of multiple treatments intra-day and low power intensities utilized;
(2) Avoidance of the need for surgical intervention;
(3) Achievement of even more dramatic results when ultrasound therapy is combined with use of an orthosis;
(4) Description of a specific ultrasound signal for obtaining the desired therapeutic results;
(5) The convenience and practicality of a much more effective method for therapeutically treating plantar fasciitis and related disorders, allowing much quicker resolution of the pain and discomfort, in comparison to other non-surgical methods;
(6) The ability to treat patients at home, which leads to much greater acceptance by the medical and patient communities, and also by third-party-payers; and
(7) The nature of the apparatus as described here serves best the purposes of further exploration for obtaining maximally effective signals and dosage regimens that can be correlated for the indicated objectives. The embodiments of the invention as described above can explore a wide range of experimental configurations. Their use is expected to lead to the development of even more compact and efficient apparatus for obtaining the indicated objectives. For example, a compact electronic analog implementation can easily be constructed if economy and simplicity are the primary objectives. Other systems which rely on combined analog and digital electronics are more expensive, yet can be more flexible in terms of the range of applications which can be addressed (e.g., systems for a single therapeutic application to plantar fasciitis, versus systems for therapeutic applications to other anatomical sites for general enthesopathies disorders). Further, systems can either be built as a stand-alone unit or as part of a PC-based system.

What is claimed is:

1. A method of non-invasively therapeutically treating plantar fasciitis in a foot locale in a living body, the method comprising the steps of:
   (a) providing an ultrasound transducer fed by an ultrasound pulser;
   (b) providing an ultrasound fixture to receive a foot of said living body and hold it next to said transducer,
   (c) reproducibly positioning said ultrasound transducer at said ultrasound fixture and acoustically coupling said ultrasound transducer to skin overlying said foot locale of said living body in such a way that a major portion of a plantar fascia including a portion thereof adjacent to calcaneus is exposed to ultrasound energy; and
   (d) energizing said ultrasound pulser for a prescribed time duration, to thereby produce an ultrasound signal within said plantar fascia for said prescribed time duration.

2. The method according to claim 1, wherein said ultrasound fixture has at least one transverse segment and at least one longitudinal segment.

3. The method according to claim 1, wherein said ultrasound transducer has an area of at least 4 square centimeters.

4. The method according to claim 1, wherein said ultrasound signal has a SATA power intensity of less than or equal to 250 milliwatts per square centimeter.

5. The method according to claim 1, wherein said ultrasound signal has a SATA power intensity of less than or equal to 20 milliwatts per square centimeter.

6. The method according to claim 1, wherein said prescribed time duration is more than 15 minutes.

7. The method according to claim 1, wherein said ultrasound signal is a continuous sinusoid.

8. The method according to claim 1, wherein said ultrasound signal is a pulsed sinusoid.

9. The method according to claim 1, wherein said ultrasound signal is a broadband repetitive pulse.

10. The method according to claim 1, wherein said ultrasound signal is an amplitude modulated sinusoid.

11. The method according to claim 1, wherein said ultrasound signal is a frequency modulated sinusoid.

12. The method according to claim 1, further including the step of injecting a local anesthetic into said foot locale, said injecting being performed prior to step (a).

13. The method according to claim 1, further including the step of applying a non-steroidal anti-inflammatory cream to said skin, said applying being performed prior to step.

14. The method according to claim 1, further including the step of injecting a cortico-steroid into said foot locale, said injecting being performed prior to step.

15. The method according to claim 1, wherein steps are performed a number of times per day.

16. The method according to claim 15, wherein said number of times per day is greater than or equal to two.

17. A method for non-invasively therapeutically treating plantar fasciitis in a locale of a foot in a living body, using an ultrasound transducer, an ultrasound pulser, and an orthotic device, which method comprises the steps of:
   (a) applying said orthotic device to said foot to hold said foot in dorsiflexion;
   (b) acoustically coupling said ultrasound transducer to skin overlying said locale of said foot of said living body;
   (c) connecting said ultrasound transducer to said ultrasound pulser; and
   (d) energizing said ultrasound pulser for a prescribed time duration, and producing an ultrasound signal within said locale of said foot for said prescribed time duration.

18. The method according to claim 17, wherein said ultrasound fixture has at least one transverse segment and at least one longitudinal segment.

19. The method according to claim 17, wherein said ultrasound transducer has an area of at least 4 square centimeters.

20. The method according to claim 17, wherein said ultrasound signal has a SATA power intensity of less than or equal to 250 milliwatts per square centimeter.

21. The method according to claim 17, wherein said ultrasound signal has a SATA power intensity of less than or equal to 20 milliwatts per square centimeter.

22. The method according to claim 17, wherein said prescribed time duration is more than 15 minutes.

23. The method according to claim 17, wherein steps (a–d) are performed a number of times per day.

24. The method according to claim 23, wherein said number of times per day is greater than or equal to two.

25. The method according to claim 17, wherein said locale contains a portion of a plantar fascia adjacent to a calcaneus.

26. The method according to claim 17, wherein said ultrasound signal is a continuous sinusoid.

27. The method according to claim 17, wherein said ultrasound signal is a pulsed sinusoid.

28. The method according to claim 17, wherein said ultrasound signal is a broadband repetitive pulse.

29. The method according to claim 17, wherein said ultrasound signal is an amplitude modulated sinusoid.

30. The method according to claim 17, wherein said ultrasound signal is a frequency modulated sinusoid.

31. A method of non-invasively therapeutically treating heel pain in a foot locale in a living body, the method comprising the steps of:
   (a) providing an ultrasound transducer fed by an ultrasound pulser;
   (b) providing an ultrasound fixture to receive a foot of said living body and hold it next to said transducer,
   (c) reproducibly positioning said ultrasound transducer at said ultrasound fixture and acoustically coupling said ultrasound transducer to skin overlying said foot locale of said living body; and
   (d) energizing said ultrasound pulser for a prescribed time duration, to thereby produce an ultrasound signal directed to a heel area for said prescribed time duration.

* * * * *

UNITED STATES PATENT AND TRADEMARK OFFICE
CERTIFICATE OF CORRECTION

PATENT NO.     : 6,251,088 B1
DATED          : June 26, 2001
INVENTOR(S)    : Jonathan J. Kaufman et al.

It is certified that error appears in the above-identified patent and that said Letters Patent is hereby corrected as shown below:

Column 9, claim 13,
Line 3, insert -- (b) -- after "step".

Column 9, claim 14,
Line 1, insert -- (b-c) -- after "steps".
Line 3, insert -- (b) -- after "step".

Signed and Sealed this

Twenty-sixth Day of March, 2002

*Attest:*

*Attesting Officer*

JAMES E. ROGAN
*Director of the United States Patent and Trademark Office*